United States Patent [19]

Hurst et al.

[11] Patent Number: 4,576,952

[45] Date of Patent: Mar. 18, 1986

[54] PYRAZOLOPYRIDINE DERIVATIVES AND THEIR USE AS ANTI-INFLAMMATORY AND/OR ANTI-ALLERGIC AGENTS

[75] Inventors: Jim Hurst, Sunderland; Josephine B. May, Nelson, both of England

[73] Assignee: Beecham Group p.l.c., Middlesex, England

[21] Appl. No.: 693,731

[22] Filed: Jan. 23, 1985

[30] Foreign Application Priority Data

Jan. 25, 1984 [GB] United Kingdom ................. 8401868
Nov. 28, 1984 [GB] United Kingdom ................. 8430012

[51] Int. Cl.[4] ................... A61K 31/415; A61K 31/44; C07D 471/04
[52] U.S. Cl. ..................................... 514/303; 546/119
[58] Field of Search ......................... 546/119; 514/303

[56] References Cited

FOREIGN PATENT DOCUMENTS 119774 2/1984 European Pat. Off. ............ 546/119
2519059 11/1975 Fed. Rep. of Germany ...... 546/119

OTHER PUBLICATIONS

Hylton Foster and Jim Hurst, J. Chem. Soc. Perkin Trans I, 1976 (5), 507–512.
Hylton Foster and Jim Hurst, J. Chem. Soc. Perkin Trans I, 1973, 2901.
E. Ajello, "New Synthesis of Condensed Heterocycles from Isoxazole Derivatives. II. Pyrazolo[4,3–b]pyridine", *J. Heterocycl. Chem.*, 8, pp. 1035–1037 (Dec. 1971).
F. M. Dietrich et al., Hypersensitivity in Mice. I. Induction of Contact Sensitivity to Oxazolone and Inhibition by Various Chemical Compounds", *Int. Arch. Allergy*, 38:246–259 (1970).
H. E. Foster et al., "Pyrazolopyridines. Part IV. Preparation and Tautomerism of 6–Cyano– and 6–Ethoxycarbonyl–1, 4–dihydropyrazole[4, 3–6]Pyridin–7–Ones", *J. Chem. Soc.*, Perkin Trans. I, 5, pp. 507–512 (1976).
B. A. Jakschik et al., Calcium Stimulation of a Novel Lipoxygenase", *Biochem. Biophys. Res. Comm.*, 95:103–110 (1980).
K. F. Swingle et al., "Comparison of Croton Oil and Contharidin Induced Inflammations of the Mouse Ear and their Modification by Topically Applied Drugs", *Arch. Int. Pharmacodyn.*, 254:168–176 (1981).

Primary Examiner—Henry R. Jiles
Assistant Examiner—J. Richter
Attorney, Agent, or Firm—James F. Haley, Jr.; Paul H. Ginsburg; Mary E. Bak

[57] ABSTRACT

Compounds of formula (I) and pharmaceutically acceptable salts thereof:

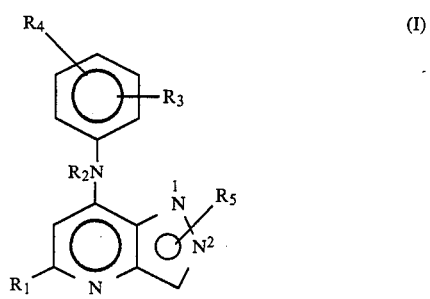

wherein:
$R_1$ is hydrogen, $C_{1-6}$ alkyl or phenyl optionally substituted by halogen, $CF_3$, $C_{1-4}$ alkoxy or $C_{1-4}$ alkyl;
$R_2$ is hydrogen or $C_{1-6}$ alkyl;
$R_3$ is hydroxy, nitro, cyano, $C_{2-10}$ acyloxy, $NR_6R_7$ wherein $R_6$ and $R_7$ are independently selected from hydrogen, $C_{1-6}$ alkyl, $C_{2-7}$ alkanoyl or $C_{1-6}$ alkylsulphonyl; or $COR_8$ wherein $R_8$ is hydroxy, $C_{1-6}$ alkoxy or $NR_9R_{10}$ wherein $R_9$ and $R_{10}$ are independently selected from hydrogen or $C_{1-6}$ alkyl;
$R_4$ is hydrogen, halogen, $CF_3$, $C_{1-4}$ alkoxy, $C_{1-4}$ alkyl or any of the groups listed for $R_3$; and
$R_5$ is hydrogen, $C_{1-4}$ alkyl or benzyl optionally substituted in the phenyl ring by halogen, $CF_3$, $C_{1-4}$ alkoxy or $C_{1-4}$ alkyl and is attached at nitrogen atom 1 or 2, having anti-inflammatory and/or anti-allergy activity, and their use as pharmaceuticals.

9 Claims, No Drawings

PYRAZOLOPYRIDINE DERIVATIVES AND THEIR USE AS ANTI-INFLAMMATORY AND/OR ANTI-ALLERGIC AGENTS

The present invention relates to pyrazolopyridines having useful pharmacological activity, to a process for their preparation and to their use as anti-inflammatories.

J. Heterocycl. Chem. 1971, 8(6), 1035–7 discloses compounds of the formula (A):

wherein R is $NH_2$, OH, $NAc_2$ or Cl. The compound wherein R is $NAc_2$ is described as having CNS antidepressant activity in mice.

A structurally distinct group of pyrazolopyridine derivatives has now been discovered which have anti-inflammatory and/or anti-allergy activity.

Accordingly, the present invention provides a compound of the formula (I) and pharmaceutically acceptable salts thereof:

wherein:

$R_1$ is hydrogen, $C_{1-6}$ alkyl or phenyl optionally substituted by halogen, $CF_3$, $C_{1-4}$ alkoxy or $C_{1-4}$ alkyl;

$R_2$ is hydrogen or $C_{1-6}$ alkyl;

$R_3$ is hydroxy, nitro, cyano, $C_{2-10}$ acyloxy, $NR_6R_7$ wherein $R_6$ and $R_7$ are independently selected from hydrogen, $C_{1-6}$ alkyl, $C_{2-7}$ alkanoyl or $C_{1-6}$ alkylsulphonyl; or $COR_8$ wherein $R_8$ is hydroxy, $C_{1-6}$ alkoxy or $NR_9R_{10}$ wherein $R_9$ and $R_{10}$ are independently selected from hydrogen or $C_{1-6}$ alkyl;

$R_4$ is hydrogen, halogen, $CF_3$, $C_{1-4}$ alkoxy, $C_{1-4}$ alkyl or any of the groups listed for $R_3$; and $R_5$ is hydrogen, $C_{1-4}$ alkyl or benzyl optionally substituted in the phenyl ring by halogen, $CF_3$, $C_{1-4}$ alkoxy or $C_{1-4}$ alkyl and is attached at nitrogen atom 1 or 2.

Suitable values for $R_1$ include hydrogen, methyl, ethyl, n- and iso-propyl and phenyl. More suitably, $R_1$ is hydrogen or methyl, preferably methyl.

Suitable values $R_2$ include hydrogen, methyl, ethyl, n- and iso-propyl. Favourably $R_2$ is hydrogen.

Suitable values for $R_3$ include hydroxy, nitro, cyano, acetoxy, propionyloxy, benzyloxy, $NR_6^1R_7^1$ wherein $R_6^1$ and $R_7^1$ are independently selected from hydrogen, methyl, ethyl, n- and iso-propyl, acetyl, propionyl, methylsulphonyl and ethylsulphonyl; $COR_8^1$ wherein $R_8^1$ is hydroxy, methoxy, ethoxy or $NR_9^1R_{10}^1$ wherein $R_9^1$ and $R_{10}^1$ are independently selected from hydrogen, methyl, n- and iso-propyl. Favourable values for $R_3$ include hydroxy, nitro, cyano, carboxy and ethoxycarbonyl. $R_3$ is favourably in the 3- or 4-position, preferably in the 4-position. $R_3$ is preferably 4-hydroxy.

Suitable values for $R_4$ include fluoro, chloro, bromo, $CF_3$, methoxy, ethoxy, n- and iso-propoxy, methyl, ethyl, n- and iso-propyl and any of the suitable groups listed for $R_3$. $R_4$ is preferably hydrogen.

Suitable values for $R_5$ include hydrogen, methyl, ethyl, n- and iso-propyl and benzyl. More suitably $R_5$ is hydrogen or 2-methyl. Favourably $R_5$ is hydrogen. It will be appreciated that when $R_5$ is hydrogen the compounds of formula (I) exist as tautomers, i.e. the $R_5$ hydrogen atom is labile. The compounds wherein the $R_5$ hydrogen is attached at the 1- or 2-position are therefore of formulae (IIa) and (IIb) respectively:

The predominant tautomeric form is of formula (IIa).

The compounds of the formula (I) can form acid addition salts with acids, such as the conventional pharmaceutically acceptable acids, for example hydrochloric, hydrobromic, phosphoric, acetic, fumaric, salicylic, citric, lactic, mandelic, tartaric and methanesulphonic.

There is a group of compounds within formula (I) wherein $R_4$ is a hydrogen, $R_5$ is hydrogen, $C_{1-4}$ alkyl or benzyl and $R_1$, $R_2$ and $R_3$ are as defined in formula (I).

There is a favourable group of compounds within formula (I) of formula (III):

wherein $R_2^1$ is hydrogen or methyl, $R_5^1$ is hydrogen or 2-methyl, and $R_3$ is as defined in formula (I).

Suitable and preferred values for $R_2^1$, $R_5^1$ and $R_3$ are as described for the relevant variables under formula (I).

A favourable sub-group of compounds within formula (III) is of formula (IV):

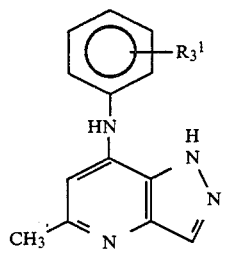

wherein $R_3^1$ is hydroxy, cyano, carboxyl, ethoxycarbonyl or nitro.

Preferably $R_3^1$ is attached at the the 3- or 4-position, most preferably the 4-position. Preferred values for $R_3^1$ are cyano and hydroxy, most preferably 4-hydroxy.

The present invention also provides a process for the preparation of a compound of formula (I) or a pharmaceutically acceptable salt thereof, which process comprises the reaction of a compound of formula (V):

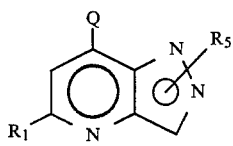

wherein Q is a leaving group and $R_1$ and $R_5$ are as defined in formula (I), with a compound of formula (VI):

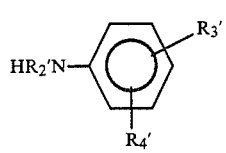

wherein $R_2'$ is $R_2$ or a group or atom convertible thereto and $R_3'$ and $R_4$ and $R_3$ and $R_4$ respectively or a group or atom convertible thereto; and thereafter optionally converting $R_2'$ to $R_2$, $R_3'$ to $R_3$, $R_4'$ to $R_4$ and/or an $R_5$ hydrogen to an $R_5$ C$_{1-6}$ alkyl group and/or forming a pharmaceutically acceptable salt thereof.

Suitable leaving groups Q include halogens such as chloro and bromo, preferably chloro.

The reaction may be carried out under conventional conditions for nucleophilic aromatic displacements, at elevated temperatures using excess of reagent as solvent (eg aniline) or in an inert solvent such as toluene, ethanol, dimethylformamide, dimethylsulphoxide or dioxan.

Conversion of an $R_2$ hydrogen to an $R_2$ C$_{1-6}$ alkyl group may be carried out by conventional amine alkylation or acylation (e.g. formylation) followed by reduction.

Conversions of $R_3'/R_4'$ to $R_3/R_4$ are generally known in the art of aromatic chemistry. Examples of such conversions are as follows:

(a) an hydroxy group may be converted to acyloxy by conventional acylation procedures, preferably using the acid anhydride in trifluoroacetic acid at elevated temperature;

(b) a cyano group may be converted to carboxy by base catalysed hydrolysis; preferably using sodium hydroxide in ethanol followed by neutralisation with acid;

(c) an alkoxycarbonyl group may be converted to CONR$_8$R$_9$ by heating with the appropriate amine;

(d) a nitro group may be converted to an amino group by reduction, preferably by catalytic reduction using palladium on charcoal;

(e) an amino group may be converted to an alkylamino or acylamino group by conventional amine acylation or alkylation; the acylation is preferably carried out using an acid anhydride and the alkylation using the alkyl halide;

(f) an amino group may be converted to an R$_3$ alkylsulphonyl group by reaction with the appropriate alkylsulphonyl chloride, preferably using an acid acceptor such as triethylamine in an inert solvent such as dichloromethane.

An R$_5$ hydrogen atom may be converted to an R$_5$ C$_{1-6}$alkyl group by conventional alkylation procedures.

It will be appreciated that these conversions may take place in any desired or necessary order. Conversions involving amine substitution may also substitute an R$_5$ hydrogen which therefore may need to be protected using an amine protecting group.

Pharmaceutically acceptable salts of the compounds of formula (I) may be formed conventionally by reaction with the appropriate acid.

Compounds of the formula (V) are either known compounds or can be prepared by analogy with processes for preparing structurally similar known compounds.

For example, compounds of the formula (V) wherein Q is chloro may be prepared by the phosphorus oxychoride chlorination of a compound of formula (VII):

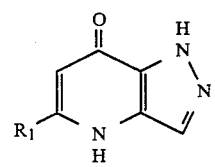

Compounds of the formula (VII) may be prepared as described in J. Chem. Soc. Perkin Trans. I, 1976 (5), 507 or by analogous methods thereto.

It will be appreciated that the compounds of formula (VII) wherein R$_5$ is hydrogen exist in the predominant tautomeric form of formula (VIIa):

In a further aspect the invention provides a pharmaceutical composition which comprises a compound of formula (I) or a pharmaceutically acceptable salt thereof and a pharmaceutically acceptable carrier.

The compositions may be adapted for administration via the topical, oral, rectal or injection routes.

The anti-inflammatory compositions of this invention may contain diluents, binders, fillers, disintegrants, flavouring agents, colouring agents, lubricants and, preservatives in conventional manner.

These conventional excipients may be employed in conventional manner, for example as in the preparation of compositions of ketoprofen, indomethacin, naproxen, acetylsalicylic acid or other anti-inflammatory agents.

The compounds of the invention have topical anti-inflammatory activity and therefore will normally be made up into a cream, lotion, gel or ointment for topical administration to the skin comprising a compound of the formula (I) which has been formulated as a cream, lotion, gel or ointment.

Cream, lotion gel or ointment formulations that may be used for compounds of the formula (I) are conventional formulations well known in the art, for example, as described in standard text books of pharmaceutics and cosmetics, such as Harry's Cosmeticology published by Leonard Hill Books, and the British Pharmacopoeia. A standard emulsifying ointment base or anhydrous polyethylene glycol are simple examples of such suitable formulations.

These compositions may be used in the topical treatment of atopic and contact dermatitis, psoriases, acne, eczema and other inflammatory dermatoses and inflammatory conditions of eyes, ears, nose and throat.

It will be appreciated that the amount of compound of the formula (I) used will depend on a number of factors such as the nature and severity of the disorder being treated, and the specific compound being used. However, by way of illustration it is believed that effective therapy can be achieved using roughly similar amounts of the compounds of formula (I) as would be used of hydrocortisone. A typical formulation will suitably contain 0.1 to 20%, more suitably 0.5 to 5% of the compound of formula (I).

A composition of this invention is useful in the treatment of rheumatism and arthritis and in the treatment of pain and other inflammatory conditions and also in the treatment of the propylaxis of bronchial asthma, rhinitis, hay fever and allergic eczema.

Suitably the oral compositions of this invention will be in the form of a unit dose such as a tablet, capsule or reconstitutable powder in a sachet. Such unit doses will generally contain from 10 mg to 1000 mg and more suitably will contain from about 30 mg to 500 mg for example 50 mg to 250 mg of active agent, for example about 50, 100, 150, 200, 250, 300, 350, 400, 450 or 500 mg. These compositions may be administered once or more times a day, for example 2, 3 or 4 times daily, so that the total daily dose for a 70 kg adult will usually be in the range of 100 to 3000 mg and more usually in the range 30 to 300 mg, for example, 500 to 2000 mg. Alternatively the unit dose may contain from 2-20 mg of active agent and may be administered in multiples if desired to give the preceeding daily dose.

For use in the treatment or prophylaxis of allergic disorders, in any of the preceding formulations, a suitable dosage unit may contain 0.01 to 500 mg of active ingredient, more suitably 1 to 500 mg for use via the oral route, 0.01 to 10 mg via inhalation, which is preferred. The effective dose of compound depends on the particular compound employed, the condition of the patient and the frequency and route of administration, but in general is in the range of from 0.001 mg/day to 100 mg/day per kilogram of the patient's body weight.

No adverse toxicological effects are observed at any of the aforementioned dosage ranges.

Where appropriate, small amounts of other anti-asthmatics and bronchodilators, for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included.

A particular composition of the invention for inflammatory diseases is a hard gelatin capsule containing the required amount of a compound of the invention in the form of a powder or granulate in intimate mixture with a lubricant, such as magnesium stearate, a filler, such as microcrystalline cellulose, and a disintegrant, such as sodium starch glycollate.

Preparations especially suitable for administration to the respiratory tract include, for example, a snuff, an aerosol, a solution for a nebulizer, or a microfine powder for insufflation, alone or in combination with an inert carrier such as lactose. In such a case the particles of active compound suitably have diameters of less than 50 microns, preferably less than 10 microns.

A favoured form of oral composition of this invention is a tablet containing the active agent. The active agent may be in the form of a recompressed granulate of the active ingredient in intimate mixture with a lubricant such as magnesium stearate, a filler such as microcrystalline cellulose and a disintegrant such as sodium starch glycollate.

For parenteral administration, fluid unit dosage forms are prepared utilising a compound of the formula (I) or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. Parenteral suspensions are prepared in substantially the same manner, except that the compound is suspended in the vehicle instead of being dissolved and sterilised by exposure to ethylene oxide before suspension in a sterile vehicle. Advantageously, a surfactant or wetting agent is included in the composition to facilitate uniform distribution of the compound.

The compositions for topical treatment may also contain other therapeutic agents such as anti-infective and/or anti-viral agents. Suitable anti-infective agents include the topically applicable antibacterial, anti-yeast, anti-fungal and anti-herpes agents already in use in topical anti-inflammatory preparations.

The invention further provides a method of treatment or prophylaxis of inflammatory and/or allergic conditions in mammals including man which comprises the administration of a compound of formula (I) or a pharmaceutically acceptable salt thereof to the sufferer.

The invention also provides a compound of formula (I) or a pharmaceutically acceptable salt thereof for use in treating inflammatory and/or allergic conditions in mammals.

Mammals which may be thus treated include humans and domestic animals such as dogs, cats or horses.

Most suitably the medicament will be administered orally as 1, 3 or 4 doses per day at the dose level previously indicated.

The following Examples illustrate the invention and the following Descriptions illustrate the preparation of intermediates thereto.

DESCRIPTION 1

(a) 4-NITROPYRAZOLE

Pyrazole (20 g) was dissolved in concentrated sulphuric acid (150 cm$^3$). The solution was kept below 10° C. and stirred whilst a mixture of concentrated sulphuric acid (120 cm³) and concentrated nitric acid (120 cm³) was added dropwise. After addition of the acid the solution was gradually heated to a temperature of 120° C. and maintained at this temperature for 24 h, cooled, added to ice, basified with 20% w/v sodium carbonate, 33% w/v, ammonia and 50% w/v sodium hydroxide. The solution was extracted with ether to yield the crude product. Crystallisation from ethyl acetate (24 g, 66%) gave white plates m.p. 166°–168°. $\nu$ max, 3180, 3130 (both sharp, medium intensity, N—H stretch), 1580, 1540, 1500, 1410, 1290, 995, 940, 815 and 756 cm⁻¹.

(b) ETHYL 3-(PYRAZOL-4-YLAMINO)CROTONATE[1]

4-Nitropyrazole (1.13 g), 10% palladium-charcoal (0.14 g), and methanol (40 cm³) were shaken with hydrogen at 5 atm for 3 h. Filtration and evaporation yielded the crude 4-aminopyrazole which was treated with ethyl acetoacetate (1.43 g) and concentrated hydrochloric acid (0.2 cm³). The mixture was heated on a steam bath for 5 min. to yield an oily solid. Trituration with aqueous ethanol gave the crotonate (1.31 g, 67%). Crystallisation from benzene-cyclohexane gave needles, m.p. 119°–120°. $\nu$ max 3400–2500 (N—H), 1650 (C=O), 1620, 1260 (C—O), and 1160 cm⁻¹.

(c) 1,4-DIHYDRO-5-METHYLPYRAZOLO 4,3-b PYRIDIN-7-ONE[1]

[1]H. E. Foster and J. Hurst. J. Chem. Soc., Perkin I, p 511 (1976).

Ethyl 3-(pyrazol-4-ylamino)crotonate (1.5 g) was added to boiling Dowtherm A (75 cm³). The mixture was heated under reflux for 15 min. allowed to cool, and on dilution with light petroleum (b.p. 60°–80° C.) gave the pyrazolopyridone (0.78 g, 68%). The pyrazolpyridone was washed thoroughly with boiling light petroleum and crystallised from aqueous ethanol (charcoal) to give prisms, mp 330°.

M+ 149.0591

$\nu$ max. 3500–2500 (N—H), 1605 (C=O), 1555, 1520, 1415 1265 and 945 cm⁻¹.

$\tau$ (CF₃—COOH) 1.43 (1H, s, 3H), 2.78 (1H, s, 6-H) and 7.10 (3H, s, CH₃).

(d) 7-CHLORO-5-METHYL-1H-PYRAZOLO(4,3-b)PYRIDINE 1,4-Dihydro-5-methylpyrazolo[4,3-b]pyridin-7-one (5 g) was dried and refluxed in phosphorus oxychloride (30 ml), in dry apparatus, for 3 h. Evaporation of the solvent, followed by neutralisation with 10% w/v sodium carbonate solution gave a grey suspension. Filtration gave the chloro-compound (5 g, 89%). Sublimation (0.1 mm Hg, 120° C.) and crystallisation from ethyl acetate-ethanol (charcoal) gave white amorphous crystals m.p. 218°. $\nu$ max. 3250–3000 (broad, N—H stretch), 1560 (N—H, bend), 1310, 1280, 1160, 940, 880, 850, 825 and 758 cm⁻¹.

$\delta$ (CF₃COOH) 2.99 (3H, s, 5-CH₃), 7.74 (1H, s, 6-H) and 8.51 (1H, s, 3-H). Total proton count 5.

Found: C, 49.89; H, 3.69; N, 25.27. C₇H₆N₃Cl requires C, 50.16; H, 3.62; N, 25.08; Cl 21.18%.

DESCRIPTION 2
7-CHLORO-1,5-DIMETHYL-1H-PYRAZOLO(4,3-b)PYRIDINE and 7-CHLORO-2,5-DIMETHYL-2H-PYRAZOLO(4,3-b)PYRIDINE A solution of methyl iodide (9.4 g) in ether (20 ml) was added to a boiling suspension of 7-chloro-5-methyl-1H-pyrazolo(4,3-b)pyridine (10 g) and sodium hydroxide (3.58 g) in 90% aqueous ethanol (20 ml) and the mixture was heated under reflux for 3 h. The solvent was removed in vacuo and the residue was extracted with boiling chloroform. The extract was dried (MgSO₄) and the solvent removed to give a mixture of the 1-methyl and 2-methyl compounds (11 g). The mixture (5.5 g) was separated by flash column chromatography using a column of 50 mm diameter, a 10″ length of silica, and ethyl acetate as eluant; 50 ml fractions were collected. Fractions 8 to 24 gave the 1-methyl compound (3.45 g, 64%) which was sublimed (0.1 mm Hg, 120°) and then crystallised from ethyl acetate to yield white prisms, m.p. 119°–121°.

$\lambda_{max}$ (MeOH) 276 (log $\epsilon$ 3.74) and 304 nm (3.71)

$\nu_{max}$ 1540, 1500, 1340, 1320, 1245, 1105, 990, 890, 875, 825 cm⁻¹.

$\delta$ (CF₃COOH) 3.08 (3H, s, 5-CH₃), 4.68 (3H, s, 1-CH₃), 7.96 (1H, s, 6-H), 8.65 (1H, s, 3-H), total proton count 8.

Found: C, 52.9, H, 4.6; N, 23.1, Cl, 19.8. C₈H₈N₃Cl, Requires: C, 52.9; H, 4.45; N, 23.1; Cl, 19.5%.

Fractions 25–37 gave no product. The column was stripped with methanol to yield the 2-methyl compound (1.75 g, 32%) which was sublimed (0.1 mm Hg, 120°) and crystallised from ethyl acetate to yield white needles, m.p. 135°–136°.

$\lambda_{max}$ (MeOH), 285 (log $\epsilon$ 4.49) and 307 nm (3.73)

$\nu_{max}$ 3100, 1535, 1180, 990, 900, 860, 850, 815, 760, 655 cm⁻¹.

$\delta$ (CF₃COOH) 3.05 (3H, s, 5-CH₃), 4.57 (3H, s, 2-CH₃), 7.86 (1H, s, 6-H), 8.70 (1H, s, 3-H), total proton count 8.

Found: C, 52.8; H, 4.6; N, 22.9; Cl, 19.5. C₈H₈N₃Cl Requires: C, 52.9; H, 4.45; N, 23.1; Cl, 19.5%.

DESCRIPTION 3
(a) 4,7-Dihydro-7-oxo-1H-pyrazolo[4,3-b]pyridine-6-carboxylic acid

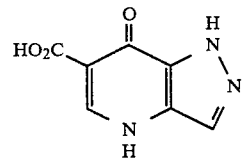

A mixture of ethyl 4,7-dihydro-7-oxo-1H-pyrazolo[4,3-b]pyridine-6-carboxylate[1] (9.0 g, 43.5 mmol) and sodium hydroxide (3.65 g, 91 mmol) in water (60 ml) and methanol (5 ml) was heated under reflux for 90 min, then cooled, diluted with water (70 ml) and adjusted to pH6 with 5N hydrochloric acid. The precipitated solid was collected, washed with water and dried to give the title compound as an off-white solid (7.0 g, 90%), m.p. >330° C. (sublimes).
[1]H. E. Foster and J. Hurst, J. Chem. Soc., Perkin Trans. 1, 1976, 507.

(b) 4,7-Dihydro-7-oxo-1H-pyrazolo[4,3-b]pyridine

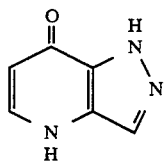

4,7-Dihydro-7-oxo-1H-pyrazolo[4,3-b]pyridine-6-carboxylic acid (7.0 g, 39 mmol) was suspended in Dowtherm A (250 ml) and the mixture was heated under reflux under nitrogen for 2.5 h. After cooling, the mixture was diluted with 60°–80° petrol and filtered. The precipitate was washed well with petrol and dried to give the crude product as an off-white solid (3.9 g, 74%). Recrystallisation from aqueous ethanol/ether gave the title compound as very fine needles, m.p. >320° C.

δ (DMSO-d$_6$): 6.0 (1H, d, J=7 Hz), 7.75 (1H, d, J=7 Hz), 7.85 (1H, s), 11.85 (1H, bs), 13.60 (1H, bs).

λ$_{max}$ (MeOH): 298 and 307 nm.

(c) 7-Chloro-1H-pyrazolo[4,3-b]pyridine

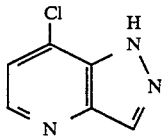

A solution of 4,7-dihydro-7-oxo-1H-pyrazolo[4,3-b]pyridine (2.0 g, 14.8 mmol) in phosphorus oxychloride (20 ml) was heated under reflux for 90 min. The excess reagent was removed in vacuo, and the residue was made slightly basic with saturated sodium hydrogen carbonate, and filtered to give a green solid. The solid was extracted with boiling ethyl acetate (2×150 ml), and the solvent was evaporated to leave the chloride as a white solid (1.55 g, 68%), m.p. >320° C.

δ (DMSO-d$_6$): 7.55 (1H, d, J=5 Hz), 8.45 (1H, s), 8.47 (1H, d, J=5 Hz).

λ$_{max}$ (MeOH): 291 nm.

EXAMPLE 1

7-(4-Cyanoanilino)-5-methyl-1H-pyrazolo[4,3-b]pyridine (E1)

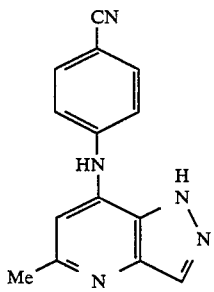

7-Chloro-5-methyl-1H-pyrazolo[4,3-b]pyridine (4 g, 0.024 mole) was heated at reflux under nitrogen with 4-aminobenzonitrile (9.44 g, 0.08 mole) in dry xylene (25 ml) for 8 h. The resulting yellow crystalline solid was collected and washed repeatedly with ethyl acetate. This solid was recrystallised from methanol/ethyl acetate to give yellow needles (2.96 g, 43%) of the required product as its hydrochloride salt. A sample of this material (500 mg) was neutralised by dissolving with warming in the minimum volume of water/methanol and adding sufficient 10% sodium hydroxide to give a pH of 8. The resulting flocculant precipitate was collected, washed with water and dried to give a pale yellow solid (408 mg, 94%) which was recrystallised from ethyl acetate/methanol to give the title compound as the free base, m.p. 280°–282° C. (decomposition).

(Found: C, 66.13; H, 4.28; N, 27.81. C$_{14}$H$_{11}$N$_5$.0.25H$_2$O requires C, 66.26; H, 4.57; N, 27.59%).

δ (DMSO-d$_6$): 2.52 (3H, s), 7.08 (1H, s), 7.54 (2H, d, J=9 Hz), 7.81 (2H, d, J=9 Hz), 8.10 (1H, s), 10.10 (1H, broad s).

Found M+ 249.1015, C$_{14}$H$_{11}$N$_5$ requires 249.1014.

EXAMPLE 2

4-[(5-Methyl-1H-pyrazolo[4,3-b]pyridin-7-yl)amino]-benzoic acid

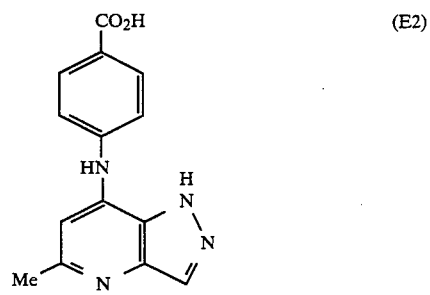

The nitrile of Example 1 (1 g, 0.004 mole) in 10% sodium hydroxide (7 ml) and ethanol (7 ml) was heated at reflux under nitrogen for 3 h. As no change was observed by uv spectroscopy a further quantity of base [40% NaOH (4 mls)] was added and heating continued for a further 3 h. After cooling the solution was extracted with ethyl acetate (3×25 ml). The aqueous layer was acidified to pH7 with dilute hydrochloric acid to give the title compound as a yellow precipitate which was collected, washed with water and dried (0.98 g, 91%), m.p. 238°–241° C.

δ (DMSO-d$_6$): 2.55 (3H, s), 7.02 (1H, s), 7.50 (2H, d, J=8 Hz), 8.00 (2H, d, J=8 Hz), 8.25 (1H, s), 10.35 (1H, broad s), 13.83 (1H, broad s).

Found M+ 268.0944. C$_{14}$H$_{12}$N$_4$O$_2$ requires 268.0960.

EXAMPLE 3

7-(4-Carbethoxyanilino)-5-methyl-1H-pyrazolo[4,3-b]pyridine (E3)

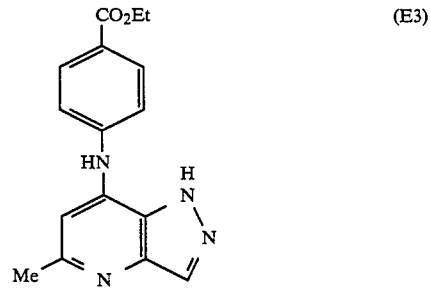

The carboxylic acid (E2) of Example 2 (0.5 g, 0.0019 mole) was heated at reflux in ethanol (25 ml) to which several drops of a saturated ethanol solution of hydrogen chloride had been added. Dimethyl sulphoxide (5.5 ml) was added after 1½ h to aid solution and heating continued for a further 7¼ h. The solution was filtered and solvent removed under reduced pressure. Ether and a small amount of ethyl acetate were added and the resulting yellow solid (518 mg, 94%) collected, m.p. 247°-250° C.

δ (DMSO-d$_6$): 1.33(3H, t, J=7 Hz), 2.51(3H, s), 4.3(2H, q, J=7 Hz), 7.03(1H, s), 7.37(2H, d, J=8 Hz), 8.00(2H, d, J=8 Hz), 8.12(1H, s), 9.05(1H, br, s), 12.72(1H, br, s).

Found M+ 296.1283. C$_{16}$H$_{16}$N$_4$O$_2$ requires 296.1273.

EXAMPLE 4

7-(4-Hydroxyanilino)-5-methyl-1H-pyrazolo[4,3-b]pyridine (E4)

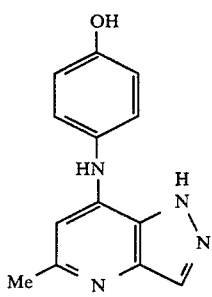
(E4)

7-Chloro-5-methyl-1H-pyrazolo[4,3-b]pyridine (0.5 g, 3 mmol) and 4-aminophenol (0.65 g, 6 mmol) in dry xylene (5 ml) were heated under reflux under nitrogen for 7 h. The resulting solid was collected and washed with water and ethyl acetate, then crystallised from methanol/ethyl acetate to give the hydrochloride salt of the required product (393 mg, 47%), m.p. 308°-310° C. (dec.).

The hydrochloride salt (355 mg, 1.28 mmol) was dissolved in water (20 ml) and methanol (10 ml) and the solution was adjusted to pH7 with 10% sodium carbonate, to give the title compound as yellow needles (283 mg, 92%), m.p. 174°-176° C.

(Found: C, 59.30; H, 5.36; N, 21.24. C$_{13}$H$_{12}$N$_4$O.1.25.H$_2$O requires C, 59.42 H, 5.56; N, 21.32).

δ (DMSOd$_6$): 2.4 (3H, s), 6.5 (1H, s), 6.8 (2H, d, J=9 Hz), 7.2 (2H, d, J=9 Hz), 8.0 (1H, s).

EXAMPLE 5

7-(3-Hydroxyanilino)-5-methyl-1H-pyrazolo[4.3-b]pyridine (E5)

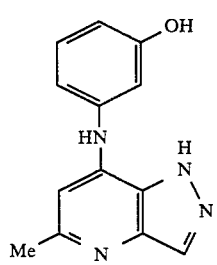
(E5)

The hydrochloride salt of the title compound was prepared by the method given in Example 1 using 3-hydroxyaniline as the nucleophile and a reaction time of 3½ h. The product was recrystallised from ethanol/ethyl acetate with charcoal decolourisation to give yellow crystals (36%), m.p. 272°-276° C. (decomposition).

(Found: C, 56.24; H, 4.83; N, 20.00. C$_{13}$H$_{12}$N$_4$O.HCl requires C, 56.43; H, 4.73; N, 20.25%).

The salt (250 mg) was dissolved in water/methanol and neutralised with 10% sodium carbonate to give a pale yellow solid, which was collected, washed with water and dried to give the free base as a yellow solid (128 mg, 59%), m.p. 158°-159° C.

δ (CF$_3$CO$_2$D): 2.75 (3H, s), 6.97 (1H, s), 7.00-7.75 (4H, m), 8.47 (1H, s).

Found M+ 240.1008. C$_{13}$H$_{12}$N$_4$O requires 240.1011.

EXAMPLE 6

7-(4-Nitroanilino)-5-methyl-1H-pyrazolo[4,3-b]pyridine (E6)

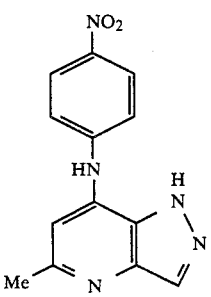
(E6)

The hydrochloride salt of the title compound was prepared by the method given in Example 1 using p-nitroaniline as the nucleophile with a reaction time of 18 h. The resulting yellow solid was collected and recrystallised from methanol/ethyl acetate to give yellow crystals (47%), m.p. 280°-285° C. (decomposition).

This hydrochloride salt was neutralised as outlined in Example 1 to give the free base as a yellow solid, m.p. 298°-302° C. (decomposition).

(Found: C, 57.16; H, 4.13; N, 25.26. C$_{13}$H$_{11}$N$_5$O$_2$.¼H$_2$O requires C, 57.09; H, 4.15; N, 25.60%).

δ (CF$_3$CO$_2$D): 2.82 (3H, s), 7.13 (1H, s), 7.78 (2H, d, J=9 Hz), 8.52 (1H, s), 8.56 (2H, d, J=9 Hz).

Found M+ 269.0920. C$_{13}$H$_{11}$N$_5$O$_2$ requires 269.0913.

EXAMPLE 7

7-(2-Hydroxyanilino)-5-methyl-1H-pyrazolo[4,3-b]pyridine (E7)

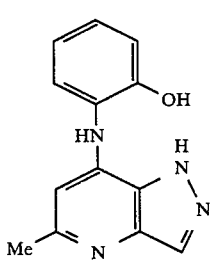
(E7)

The hydrochloride salt of the title compound was prepared by the method given in Example 1 using 2-hydroxyaniline as the nucleophile with a reaction time of ¾ h. The resulting brownish yellow solid was collected and washed with ether before extracting (x3), with hot ethyl acetate leaving a greyish solid which was recrystallised from methanol/ethyl acetate to give the required hydrochloride salt as an off-white solid (60%) m.p. 290°-295° C. (decomposition).

The above salt (309 mg) was neutralised by the method given in Example 1 to give the free base as a yellow solid (253 mg, 94%), m.p. 262°-263° C. (decomposition).

(Found: C, 65.07; H, 4.96; N, 23.41. $C_{13}H_{12}N_4O$ requires C, 64.99; H, 5.03; N, 23.32%).

δ(DMSO-$d_6$): 2.38 (3H, s), 6.5 (1H, s), 6.7-7.1 (3H, m), 7.3-7.5 (1H, m), 7.85 (1H, br.s), 8.03 (1H, s), 12.75 (1H,br.s). Found M+ 240.1021. $C_{13}H_{12}N_4O$ requires 240.1011.

EXAMPLE 8

1,5-Dimethyl-7-(3-hydroxyanilino)-1H-pyrazolo[4,3-b]pyridine (E8)

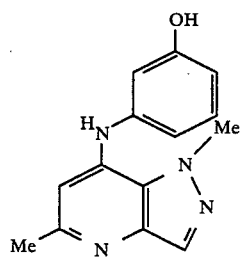
(E8)

The title compound was prepared by the method given in Example 1 with a reaction time of 1.75 h. The free base was obtained as a white solid, m.p. 264°-265° C. by neutralisation of the hydrochloride salt.

δ (DMSO-$d_6$): 2.43 (3H, s), 4.15 (3H, s), 6.3-6.7 (3H, m), 6.82 (1H, s), 6.95-7.3 (1H, m), 7.99 (1H, s), 8.15 (1H, br.s), 9.4 (1H, br.s).

EXAMPLE 9

7-(4-Hydroxyanilino)-1H-pyrazolo[4,3-b]pyridine hemihydrate (E9)

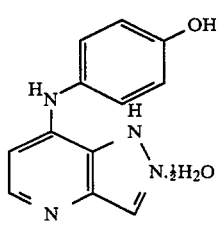
(E9)

A mixture of 7-chloro-1H-pyrazolo[4,3-b]pyridine (0.50 g, 3.26 mmol) and 4-aminophenol (0.71 g, 6.52 mmol) in xylene (10 ml) was heated under reflux under nitrogen for 5 h. After cooling the reaction mixture, the solid was collected and washed well with ethyl acetate and water. The solid was then dissolved in warm aqueous methanol, and the solution was adjusted to pH 8 with saturated sodium bicarbonate solution. The product separated as needles, which were recrystallised from aqueous methanol to give the title compound (260 mg, 35%), mp 286°-296° C.

(Found: C, 61.59; H, 4.63; N, 23.69. $C_{12}H_{10}N_4O.\frac{1}{2}H_2O$ requires C, 61.26; H, 4.71; N, 23.82%).

δ (DMSO-$d_6$): 6.60 (1H, d, J=6 Hz), 6.80 (2H, d, J=9 Hz), 7.20 (2H, d, J=9 Hz), 8.15 (1H, s), 8.15 (1H, d, J=6 Hz), 8.3 (1H, broad s).

EXAMPLE 10

7-(4-Dimethylaminoanilino)-5-methyl-1H-pyrazolo[4,3-b]pyridine. (E10)

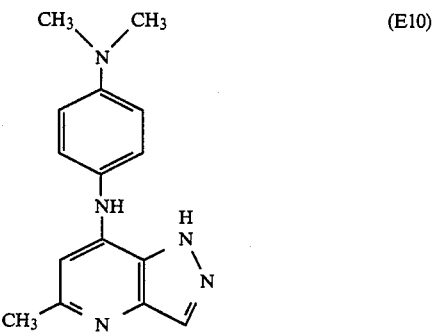

7-Chloro-5-methyl-1H-pyrazolo[4,3-b]pyridine (1 g), freshly prepared 4-dimethylaminoaniline (0.8 g), and absolute ethanol (20 ml) were heated under reflux in dry conditions in an atmosphere of nitrogen for 18 h. The solvent was removed in vacuo, the solid obtained was suspended in water, and the pH was adjusted to 7.8. The solid was filtered off, washed with water and dried to yield the 7-(4-dimethylaminoanilino)-compound (1.3 g, 80%) which on crystallisation from ethanol gave paleyellow needles m.p. 215°-218°.

(Found: C, 67.2; H, 6.4: N, 26.4. $C_{15}H_{17}N_5$ requires C, 67.4; H, 6.4; N, 26.2%), $\nu_{max}$.3400-2500 (N—H), 1625, 1590, 1529, 1030, 942 cm$^{-1}$, δ ($CF_3COOH$) 2.80 (3H, s, 5-$CH_3$), 3.58 (6H, s, N($CH_3$)$_2$), 7.00 (1H, s, 6-H), 7.89 (4H, s, aromatic protons), 8.52 (1H, s, 3-H), 9.70 (2H, s, N⊕$H_2$), total proton count 17.

PHARMACOLOGICAL DATA

Mouse Oxazolone Screen

Compounds were tested for topical anti-inflammatory activity in a screen using the mouse sensitised to oxazolone, by a method modified from that of Dietrich and Hess [Dietrich, F. M., and Hess, R., Int. Arch. Allergy, (1970), 38, 246-259].

Mice were sensitised with oxazolone (2 mg in 20 μl ethanol) on a shaved area of the abdomen. Five days later, the animals received 10 μl THF/MeOH (1:1 v/v) on the right ear, and the test compound in the same solvent on the left ear. One hour later, the animals were challenged with 100 μg oxazolone in 10 μl acetone on each ear. Ear weights were measured 24 h later. Percentage inhibition of the inflammatory swelling refers to the increase in weight of left ears (oxazolone plus compound) compared with solvent-treated negative controls, as a proportion of the increase in weight of right ears (oxazolone alone) over similar controls.

In this test the compound of Example 4 had an ED$_{50}$ of 240 μg/ear ($r^2$=0.96).

Mouse Cantharidin Screen

Compounds were tested for topical anti-inflammatory activity in a cantharidin mouse ear screen, modified from Swingle et al [Swingle, K. F., Reiter, M. J. and Schwartzmiller, D. H., Arch. Int. Pharmacodyn., (1981), 254, 168-176].

25 μg cantharidin (in 10 μl THF/MeOH) was applied to both ears. Compound, in the same solvent, was applied at the same time, to the left ear only. Ears were weighed 24 h after cantharidin application. Percentage inhibition of the acute inflammatory swelling refers to the increase in weight of left ears (cantharidin plus compound) compared with solvent-treated negative controls, as a proportion of the increase in weight of right ears (cantharidin alone) over similar controls.

The activity of a selection of compounds of this invention is shown in Table 1.

TABLE 1

| Mouse Cantharidin Data (24 h) | | |
|---|---|---|
| Compound Example No. | % Inhibition | Concentration ($\mu$g/ear) |
| 1 | 29 | 300 |
| 4 | 71 | 200 |
| 5 | 49 | 500 |
| 8 | 31 | 278 |

RBL-1 5-Lipoxygenase Screen

5-Lipoxygenase enzyme was prepared as a 10,000 g supernatant from RBL-1 cells by the method of Jakschik [Jakschik, B. A., Sun, F. F., Lee, L. M. and Steinhoff, M. M., 1980, Biochem. Biophys. Res. Comm. 95, 103]. The 10,000 g supernatant was diluted with homogenization buffer to the equivalent of $1.5-2.5 \times 10^7$ cells ml$^{-1}$ and made 2 mM with respect to CaCl$_2$. Aliquots of 0.5 ml were then dispensed into tubes, and incubated at 29° C. with 5 $\gamma$l ethanol or compound in ethanol at the desired concentration for 2 min. Then [1-$^{14}$C] arachidonic acid was added in buffer to give a final concentration of 6.3 $\mu$m and 0.2 $\mu$Ci per incubation, and the reaction continued at 29° C. for 2 min. The reaction was terminated by adding 1 ml of acetone and cooling on ice, 0.5 ml of ice-cold saline and 10 $\mu$l of 2N formic acid were added, and the mixture was extracted with 2$\times$2 ml of chloroform. The extract was stored under N$_2$ at $-20°$ C. until analysis by chromatography. Activity was measured as the percentage of total radioactivity found in 5-HETE and 5,12-diHETE, and inhibition calculated as the decrease in formation of the sum of these two species in compound-treated incubates relative to control incubates.

In this test the compound of Example 4 gave an inhibition of 66% at a dose of 20 $\mu$M.

We claim:

1. A compound of the formula (I) and pharmaceutically acceptable salts thereof:

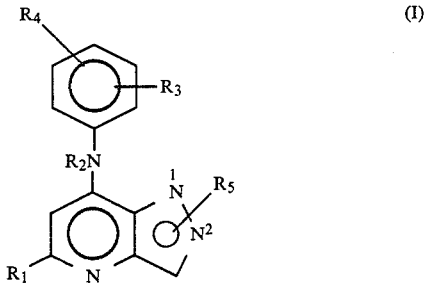

wherein:

$R_1$ is hydrogen, $C_{1-6}$ alkyl or phenyl optionally substituted by halogen, $CF_3$, $C_{1-4}$ alkoxy or $C_{1-4}$ alkyl;

$R_2$ is hydrogen or $C_{1-6}$ alkyl;

$R_3$ is hydroxy, nitro, cyano, $C_{2-10}$ acyloxy, $NR_6R_7$ wherein $R_6$ and $R_7$ are independently selected from hydrogen, $C_{1-6}$ alkyl, $C_{2-7}$ alkanoyl or $C_{1-6}$ alkylsulphonyl; or $COR_8$ wherein $R_8$ is hydroxy, $C_{1-6}$ alkoxy or $NR_9R_{10}$ wherein $R_9$ and $R_{10}$ are independently selected from hydrogen or $C_{1-6}$ alkyl;

$R_4$ is hydrogen, halogen, $CF_3$, $C_{1-4}$ alkoxy, $C_{1-4}$ alkyl or any of the groups listed for $R_3$; and $R_5$ is hydrogen, $C_{1-4}$ alkyl or benzyl optionally substituted in the phenyl ring by halogen, $CF_3$, $C_{1-4}$ alkoxy or $C_{1-4}$ alkyl and is attached at nitrogen atom 1 or 2.

2. A compound according to claim 1 of formula (III):

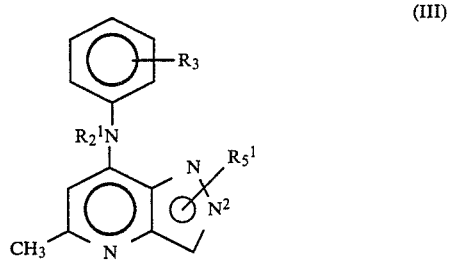

wherein $R_2'$ is hydrogen or methyl, $R_5'$ is hydrogen or 2-methyl and $R_3$ is as defined in claim 1.

3. A compound according to claim 2 of formula (IV):

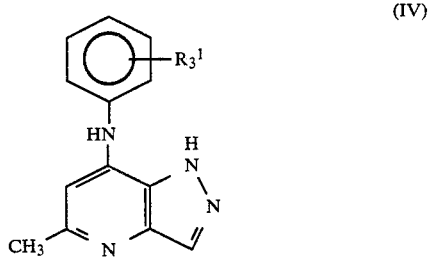

wherein $R_3'$ is hydroxy, cyano, carboxyl, ethoxycarbonyl dimethylamino or nitro.

4. A compound according to claim 3 wherein $R_3'$ is attached at the 3- or 4-position.

5. A compound selected from the group consisting of
7-(4-Cyanoanilino)-5-methyl-1H-pyrazolo[4,3-b]pyridine,
4-[(5-Methyl-1H-pyrazolo[4,3-b]pyridin-7-yl)amino]benzoic acid,
7-(4-Carbethoxyanilino)-5-methyl-1H-pyrazolo[4,3-b]pyridine,
7-(3-Hydroxyanilino)-5-methyl-1H-pyrazolo[4,3-b]pyridine,
7-(4-Nitroanilino)-5-methyl-1H-pyrazolo[4,3-b]pyridine,
7-(2-Hydroxyanilino)-5-methyl-1H-pyrazolo[4,3-b]pyridine,
1,5-Dimethyl-7-(3-hydroxyanilino)-1H-pyrazolo[4,3-b]pyridine,
7-(4-Hydroxyanilino)-1H-pyrazolo[4,3-b]pyridine and
7-(4-Dimethylaminoanilino)-5-methyl-1H-pyrazolo[4,3-b]pyridine.

6. 7-(4-Hydroxyanilino)-5-methyl-1H-pyrazolo[4,3-b]pyridine.

7. An anti-inflammatory pharmaceutical composition comprising an anti-inflammatory effective amount of a compound according to claim 1 or a pharmaceutically acceptable salt thereof and a pharmaceutically acceptable carrier.

8. A method of treatment of inflammatory conditions in mammals comprising the administration to the mammal of an anti-inflammatory effective amount of a compound according to claim 1 or a pharmaceutically acceptable salt thereof.

9. A method according to claim 8, wherein said compound is 7-(4-Hydroxyanilino)-5-methyl-1H-pyrazolo[4,3-b]pyridine.

* * * * *